United States Patent [19]
Gavish et al.

[11] Patent Number: 5,272,090
[45] Date of Patent: Dec. 21, 1993

[54] SENSOR ELEMENT FOR DETERMINING THE AMOUNT OF OXYGEN DISSOLVED IN A SAMPLE

[76] Inventors: Moshe Gavish; Misha Roitberg, both of P.O. Box 9263, Kiryat Bialik 27000, Israel

[21] Appl. No.: 861,189

[22] Filed: Mar. 31, 1992

[51] Int. Cl.$^5$ .................... G01N 21/64; G01N 33/50
[52] U.S. Cl. ................................. 436/133; 128/634; 356/402; 356/409; 356/411; 385/12; 422/82.06; 422/82.07; 422/82.08; 436/68; 436/136; 436/172
[58] Field of Search ............ 422/82.05–82.08; 436/68, 133, 136, 172; 128/634; 385/12, 13; 356/402, 409, 411

[56] References Cited
U.S. PATENT DOCUMENTS
4,639,594  1/1987  Schoch et al. .
4,849,172  7/1989  Yafuso et al. ...................... 422/56

OTHER PUBLICATIONS
Jones, et al., *Analytical Proceedings*, (Jul. 1985) vol. 22, pp. 207–210.

*Primary Examiner*—Jill A. Johnston
*Attorney, Agent, or Firm*—Morgan & Finnegan

[57] ABSTRACT

A method and apparatus are described for an accurate determination of the concentration of a gas, vapor or a gas dissolved in a sample which compensate for variations in temperature and light - source intensity. The apparatus comprises a sensor containing a fluorescent reagent connected to a transfer optic, such as fiber optics prism or glas pipes, and to a reference sensor containing the same fluorescent reagent. The reference sensor is encapsulated in an environment containing air. The light emitted from the first sensor and the reference sensor is determined and recorded automatically, the concentration of the gas being calculated based on the output from said light detectors using calibration data of the fluorescent reagent present in the sensors. The reagent is immobilized in the sensor by a glue, such as a silicon glue.

10 Claims, 3 Drawing Sheets

SENSOR ELEMENT FOR DETERMINING THE AMOUNT OF OXYGEN DISSOLVED IN A SAMPLE

The present invention relates to a method for the manufacture of a fluorescent chemical sensor for determining the concentration of gases, vapours, or dissolved gases in a sample. More particularly, the invention relates to a method for the manufacture of a fluorescent chemical sensor for determining the concentration of gases, vapours or dissolved gases in a sample, that is compensated against ambient temperature variation and variation in light-source intensity.

BACKGROUND OF THE INVENTION

Chemical sensors which use a fluorescent indicator for measurement of concentration based on emitted fluorescent intensity as a main parameter, have suffered from drift and inaccuracy results caused by changes in source intensity or ambient temperature.

The following attempts to alleviate these disadvantages have been proposed but only with a partial success.

One suggestion was that the temperature has to be measured by a thermometer and that of the source intensity by a separate detector. The measured fluorescent intensity was corrected based on Tables which have a precalibrated data set which serve for temperature compensation. However, this compensation does not cover all factors which cause drift, such as: photobleaching, variation of the reagent properties after sterilization and variations of intensity caused by other optical components of the system except the emitting source.

Another proposal was to incorporate a second fluorescent reagent that emits light at a different wavelength and is not sensitive to the measured chemical changes. However, only a partial optical compensation could be achieved which does not include the differences in spectral response of detector.

A further suggestion, was to measure the lifetime of the excited state, instead of the intensity. In this case, there is not any compensation for the ambient temperature and therefor an additional thermometer is necessary. Also, a pulsed light source with time constants in the order of magnitude like the lifetime of the excited electronic state of the fluorescent reagent must be used. The bandwidth of the detector and electronics is large, so that a corresponding large intensity of light will be required. In this manner, the method for the manufacture of this sensor is quite complicated and costly.

Another suggestion was to use the fluorescent reagent immobilized in a rigid polymer, such as plexiglass, as a reference. However, this method does not provide any compensation for differences in environmental effects on fluorescent material and actually was never used, due to the absence of complete compensation.

Japanese Kokai No. 59-170748 describes a method for determining the presence of oxygen in an environment, which consists of exposing a sensor therein and measuring the quenching related by the decrease in intensity. A reference device with areas of differing size or concentration of luminiscent material is immobilized in a support, which preferably is a polymer, that is relatively impermeable to oxygen. The indicators used consist of luminiscent inorganic materials which luminisce when excited with visible or ultraviolet light and whose luminiscence is quenchable by oxygen. The luminiscent materials which are mentioned belong to platinum group metal complexes. The luminiscent reagent on the reference element is spread in a band ranging from low to high concentrations. The measurement itself is done by comparing visually the light intensity of the signal with the light intensities of the band on the reference sensor. The main disadvantage of this method is due to the subjective determination carried out by eye, which of course can not be accurate enough. As mentioned in the specification, the precision accuracy of oxygen determination is about 2%, which actually should be considered a semiquantitative oxygen determination. Of course in those cases where a very high precision is required, this method can not be used.

It is an object of the present invention to provide a method for an accurate determination of the concentration of gases, vapours or dissolved gases in a sample. It is another object of the present invention to provide a method for an accurate determination of the concentration of gases, vapours or gases dissolved in a sample, which compensates for the variation caused by the change in concentration of the respective gas. It is yet another object of the present invention to provide a method for an accurate determination of the concentration of gases, vapours or gases dissolved in a sample, wherein said determination is objective being measured automatically.

BRIEF DESCRIPTION OF THE INVENTION

The invention relates to a method and a sensing apparatus for an accurate determination of the concentration of gases vapours or gases dissolved in a sample by providing a sensor element containing a fluorescent reagent which is connected to an optical fiber comprising at least five terminal bundles, and a reference sensor element which possesses the same fluorescent reagent, connected to the other end of said optical fiber, being insulated from the chemical environment, wherein the light emitted from the first sensor element (S) and from the reference sensor (R) are determined by light detectors and recorded, the concentration of the gas, vapour or gas dissolved being calculated automatically based on the output from said light detectors using calibration data of the fluorescent reagent present in said sensor element. In this manner, the determination of the concentration of a gas is very accurate compensation for any factors such as: ambient temperature, variation of the optical properties of the reaction, variation in source intensity caused by electrical and thermal instabilities and changes in optical fiber properties caused by changes in temperature and bending. It was found that the accuracy of the determination is very high, the precision being generally about 0.1%.

DETAILED DESCRIPTION OF THE INVENTION

According to the present invention, the sensing apparatus comprises a reference sensor which is encapsulated with a tight cover on the fluorescent reagent, thus avoiding any influence imparted by any chemical existent in the surrounding on the fluorescence emission from the reagent. The simplest solution for this encapsulation to obtain this goal is the presence of air, so that factors such as temperature, intensity and photobleaching are compensated for a prolonged period of time. One of the advantages of the method according to the present invention, is the homogeneous location of the fluorescent reagent in the reference sensor, which permits the output from the reference sensor, as received by a light detector, to be automatically converted into electric signals. In this manner, the determination of the concentration of a gas, will be much more accurate, being completely objective. Also, since the luminiscent reagent in the sensor element is the same as in the reference sensor, the emission colours will be the same so that the intensities can be easily compared.

The fluorescent reagents which are useful for the present invention are selected from the group consisting of polycyclic aromatic molecules, homocyclic and heterocyclic molecules which possess the luminiscent property. The reagent is immobilized on the sensor, using any of the known methods, the preferred one being the use of a glue, such as silicon glue.

According to one embodiment of the present invention, the AC voltage generated by the detectors is synchronically demodulated and the ratio of the DC voltages is used as a normalized intensity for the calculation of the concentration of the respective gas.

According to another embodiment of the invention, the source intensity is modulated either electronically or mechanically, so that the light intensity which reaches the signal and reference detectors, will produce an alternating current that can be easily distinguished from background illumination.

The method can be used for determining the concentration of gases, such as: oxygen, carbon dioxide in their gaseous form or dissolved in a sample. The method is also useful for the measurement of the pH of a sample. The light intensity sources to be applied, may be selected from ultraviolet or infrared wavelengths.

DETAILED DESCRIPTION OF THE DRAWINGS

Figure 1:
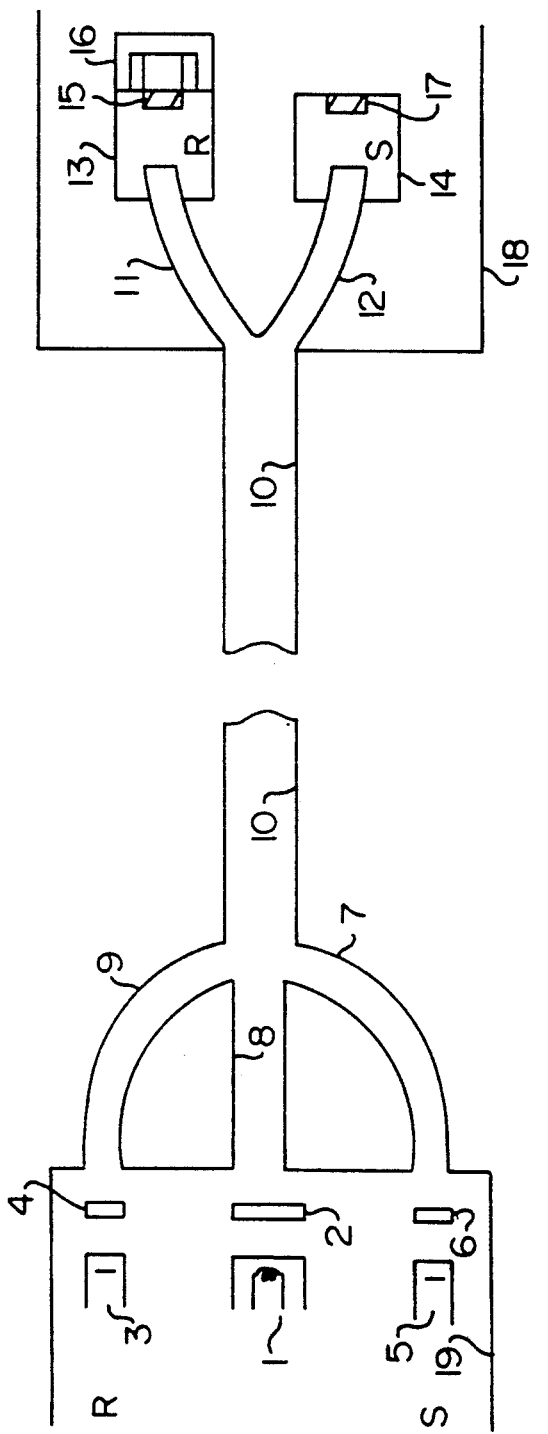
FIG. 1, is a general illustration of the apparatus.

The invention will be further illustrated by the following three Figures without being limited thereto, the Figures being presented only for a better understanding of the invention:

In FIG. 1, a light source (1) emits a radiation at a wavelength $/_1$, which passes through an optical filter (2) to a five terminal bundle (10) through the terminal (8) which contains 50% of the fibers in the instrument side (19). The light which enters through port (8) is split into two equal parts to branches (11) and (12) at the sensing head side. The branch (11) contains a reference sensor (R) with a holder (13), fluorescent reagent (15) and the encapsulator (16). The branch (12) contains the signal sensor (S) with a holder (14) and the fluorescent reagent (17). The sensing head measures the gas concentration in the chamber (18).

Part of the fluorescent radiation having a wavelength $/_2$ greater than $/_1$ is emitted back to the bundles (11) and (12). Half (50%) of the light from bundle (11) is connected to terminal (9) at the instrument side and is transmitted through the $/_2$ filter (4) and will be detected by reference detector (3). The other 50% of the light from bundle (12) is connected to terminal (7) at the instrument side and is transmitted through a second $/_2$ filter (6) and detected by detector (5). As will be realized, one may utilize instead of a fiber optic another transfer expedient, although fiber optics are most preferred.

Figure 2:
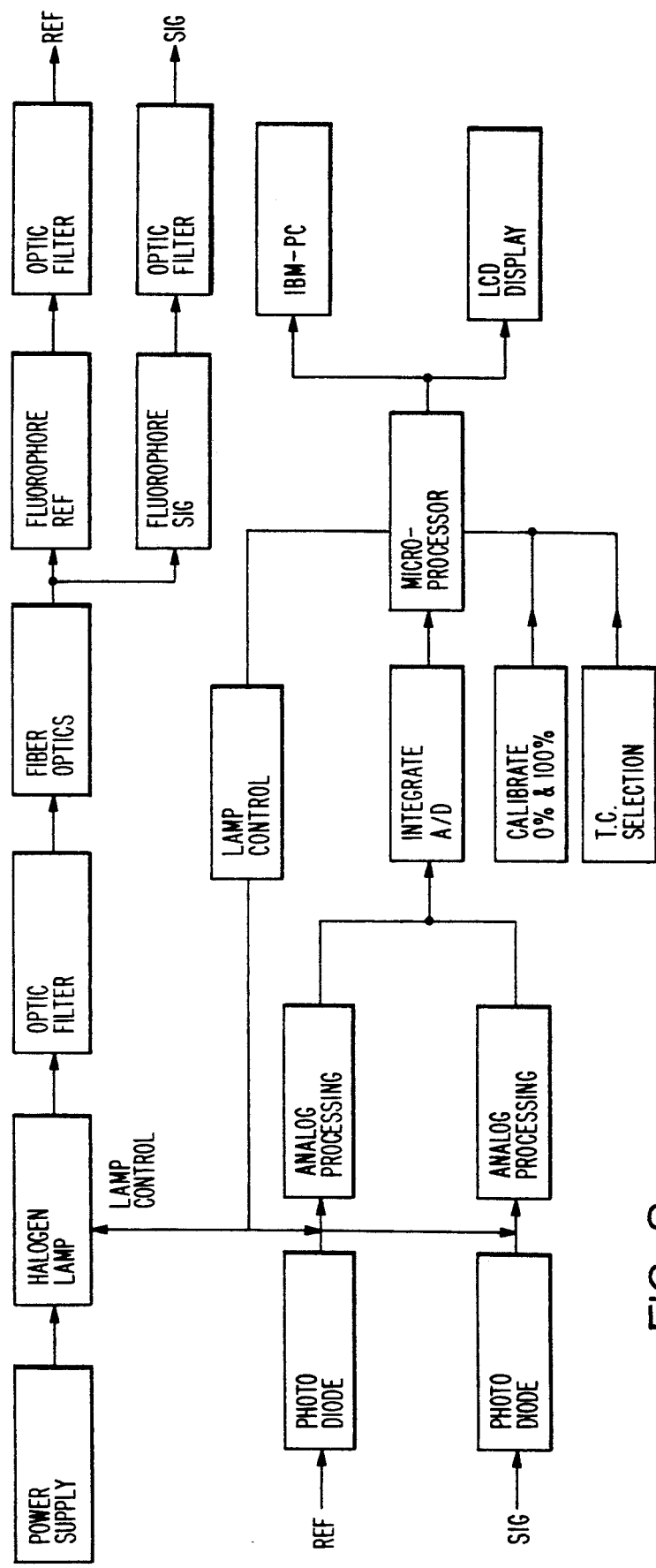
FIG. 2, is a block-diagram of a preferred embodiment of the electronic measurement and the data processing unit.

FIG. 2, illustrates a block diagram of a preferred embodiment of the electronic measurement and the data processing unit. The light source comes from a halogen lamp that is controlled from the microprocessor to set a constant frequency. The light intensities from reference sensor (R) and from the sensor element (S) are fed to two separate photodiodes, are amplified and filtered by an analog processing unit before being converted to a digital ratio by the integrate A/D. The microprocessor calculates the gas concentration based on calibration data and the properties of the fluorescent reagent. The ratio R/S is not affected by any changes in the source intensity or in the vessel temperature, the time providing instrument side electronics always being the same for the two channels.

Figure 3:
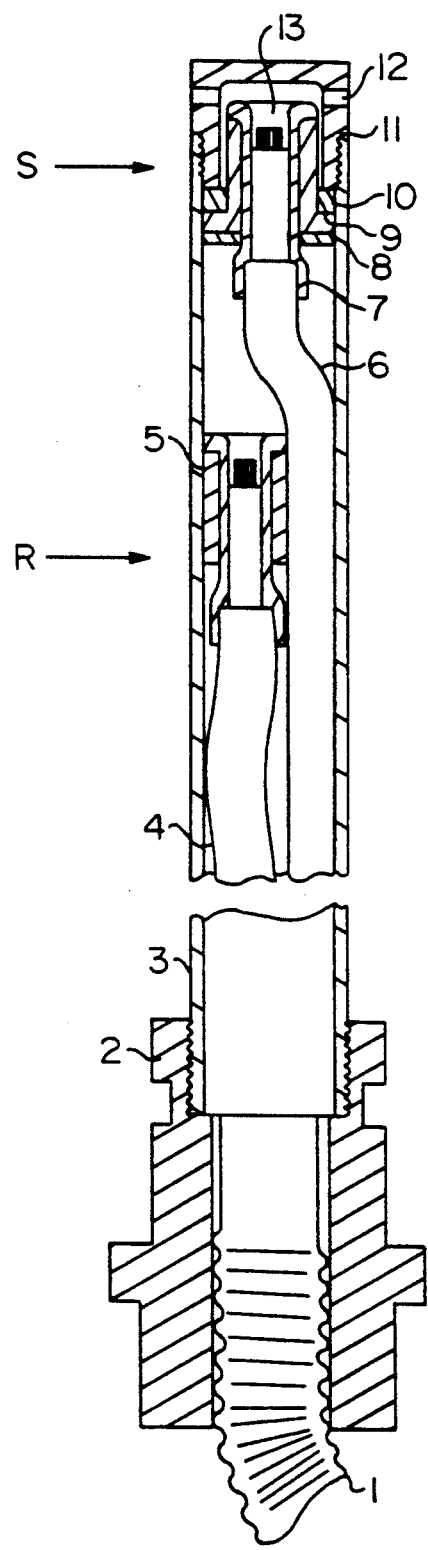
FIG. 3, is an illustration of the contact between the head of the sensor and a liquid.

FIG. 3 illustrates in a schematic manner how the head of the sensor contacts a liquid, whose oxygen content present in a vessel has to be determined. The two sensors signal (S) and reference (R) extend from protected bundle (1) which is connected to the main electronic box where the light source and detectors are operating. This bundle is split to a reference bundle (4) and a signal bundle (6). Both are housed in a fermentator adaptor (2) and a stainless steel protecting tube (3). The signal bundle ends with a ferule (7) that is connectd to the sample holder (9) by a screw. The sample holder leans against a metal washer (8) from the back side and is fastened by a stainless steel cup (11) which at the same time also presses the "O" ring (10) to block the escape of gases and vapours during operation of the fermentor. The openings on the side of the cup (12) enable free circulation of liquid above the fluorescent sample (13). The reference sensor with the fluorescent reagent is encapsulated in the compartment (5) but is located quite close to the sample so that it feels the same temperature.

Although in the above description, a fiber optic is mentioned as an optic transfer from light source to the fluorescent material and back to to the detectors R and S, one may use also other transfer media such as prisms or glass pipes.

The method and sensor element produced according to the present invention can be used for many applications, typical uses being the following:
  measuring of the oxygen in various aqueous samples.
  determining the oxygen for biochemical oxygen demand known as BOD;
  measuring the level of oxygen in blood, using a fiber-optic probe;
  measuring the oxygen level in air samples, and
  monitoring low oxygen levels in various chemical reaction vessels.

The invention will be further illustrated by the following Example with is presented for a better understanding of the invention without being limited thereto.

EXAMPLE 1

A sensor element, containing decacyclene as fluorescent reagent immobilized by a glue silicon, with a fiber optic was sued for measuring the oxygen dissolved in a vessel containing water and dissolved air. The temperature which prevail in the veseel were in the range of between 5° and 90° C., the changes occuring mainly from the various temperatures of the solutions which entered into the vessel. The method for measuring the oxygen as described above, was accurately determined for a period of one month.

Due to the various constituents of said solution, strong variations in source intensity of more than 100% were noticed. However, both these variations as well as the temperature changes, were compensated by the use of the sensor element as described above.

Reliable results were obtained even after the use of the system for one month.

We claim:

1. A method for an accurate determination of the concentration of a gas, vapour or a gas dissolved in a liquid sample comprising providing a sensing apparatus which comprises an optical fiber containing at least five terminal bundles, of which one end is divided into first, second and third terminals and a first terminal is connected to a light source and the other end is divided into fourth and fifth terminals, a sensor element containing a fluorescent reagent, and connected to the fourth terminal, the sensor element being exposed to a chemical environment, a reference sensor element containing the same fluorescent reagent and connected to the fifth terminal, the reference sensor element being insulated from the chemical environment, and first and second light detectors, the first light detector receiving light emitted from the sensor element that passes through the second and fourth terminals and the second light detector receiving light emitted from the reference sensor element that passes through the third and fifth terminals;

transmitting light through the optical fiber and measuring the concentration of the gas, vapour or gas dissolved in a liquid sample in the sensor and reference sensor elements;

transmitting light emitted by the sensor and reference sensor elements through the optical fiber and detecting the light so transmitted with the first and second light detectors and recording the output of the first and second light detectors; and automatically calculating the concentration of the gas, vapour or gas dissolved in the liquid sample based on the output from said first and second light detectors using calibration data developed from exposure of the fluorescent reagent present in the sensor and reference sensor elements to the gas, vapour or gas dissolved in a liquid sample.

2. The method according to claim 1, wherein said reference sensor element is encapsulated within a fermentation adaptor and a stainless steel protecting tube and tight covered by an O-ring, the tight cover containing air.

3. The method according to claim 1, wherein the fluorescent reagent is located homogeneously in the reference sensor element.

4. The method according to claim 1, wherein the fluorescent reagent is selected from the group consisting of polycyclic aromatic molecules which posses the luminescent property.

5. The method according to claim 1, wherein an AC voltage is generated by the first and second light detectors and the AC voltage is synchronously demodulated into DC voltages and the ratio of the DC voltages is used as a normalized intensity for the calculation of the concentration of the gas, vapour or gas dissolved in a liquid sample.

6. The method according to claim 1, wherein said gas, vapour or gas dissolved in a liquid sample is selected from oxygen, carbon dioxide or a solution containing oxygen and carbon dioxide.

7. A fluorescent measuring apparatus comprising:

a light source emitting radiation;

an optical-fiber comprising at least five terminal bundles, of which one end is divided into first, second and third terminals and the first terminal is connected to said light source and the other end of said optical-fiber is divided into fourth and fifth terminals;

a sensor element exposed to a chemical environment and connected to the fourth terminal, and reference sensor element connected to the fifth terminal, both said sensor element and said reference sensor element containing the same fluorescent reagent, the reference sensor element being insulated from the chemical environment; and first and second light detectors, the first light detector receiving light emitted from the sensor element that passes through the second and fourth terminals and the second light detector receiving light emitted from the reference sensor element that passes through the third and fifth terminals.

8. The fluorescent measuring apparatus according to claim 7, wherein said light source emits radiation in the wavelengths of ultraviolet and infrared.

9. The fluorescent measuring apparatus according to claim 7, wherein said reference sensor element is encapsulated in a housing which allows air to surround the reference sensor element.

10. The fluorescent measuring apparatus according to claim 7, further comprising means for automatically calculating the concentration of a gas, vapour or a gas dissolved in a liquid sample from the outputs of said first and second light detectors and further including means for compensating for any changes in the temperature and light source intensity.

* * * * *